United States Patent [19]

Lindquist, Sr.

[11] Plant 4,284

[45] Jul. 25, 1978

[54] HYBRID TEA ROSE PLANT

[75] Inventor: Robert V. Lindquist, Sr., Hemet, Calif.

[73] Assignee: The Conard-Pyle Company, West Grove, Pa.

[21] Appl. No.: 850,402

[22] Filed: Nov. 10, 1977

[51] Int. Cl.[2] ..... A01H 5/00

[52] U.S. Cl. ..... Plt./19

[58] Field of Search ..... Plt./18-19

*Primary Examiner*—Robert E. Bagwill

*Attorney, Agent, or Firm*—Burns, Doane, Swecker & Mathis

[57] ABSTRACT

A rose plant of the Hybrid Tea class originated by the crossing of Fragrant Cloud (U.S. Plant Pat. No. 2,574) with Miss All-American Beauty (U.S. Plant Pat. No. 2,625).

1 Drawing Figure

SUMMARY OF THE INVENTION

My invention relates to a new and distinct variety of rose plant of the Hybrid Tea class originated by me as the result of a breeding program using Fragrant Cloud (U.S. Plant Pat. No. 2,574) as seed parent and Miss All-American Beauty (U.S. Plant Pat. No. 2,625) as pollen parent. This new variety initially has been designated 75 R 14. The variety name for this new variety is "Linrick".

As a result of this crossing, I have produced a new and useful rose variety which is distinguished from its parents, and all rose varieties of which I am aware, as evidenced by the following unique combination of characteristics:

1. A Hybrid Tea rose plant bearing blooms which display a spectrum of red shades ranging from a lighter hue at the petal base to a vibrant watermelon red on the petal edge which is particularly dramatic under sunny skies.

2. A vigorous and erect growth habit.

Asexual reproduction of my new variety by budding at Hemet, Calif., shows that all characteristics of the new variety are established and transmitted through succeeding propagations.

BRIEF DESCRIPTION OF THE DRAWING

The accompanying drawing shows typical specimens of the vegetative growth and flowers of my new variety in different stages of development as depicted in color as nearly true as is reasonably possible to make the same in a color illustration of this character.

DETAILED DESCRIPTION OF THE VARIETY

The following is a detailed description of my new variety while grown in a greenhouse at Hemet, Calif., in May, 1977. Color terminology is in accordance with the Colour Chart of the Royal Horticultural Society, London, England.

Class: Hybrid Tea.

Propagation: It holds its distinguishing characteristics through succeeding propagations by budding.

FLOWER

Blooming habit: Recurrent, continuous.

Bud:

*Size.*—Large.

*Form.*—Ovoid.

*Color.*—When sepals first divide — near red — Group 53A. When petals begin to unfurl — near red — Group 53D. When half blown: Inside of petals — near red — Group 54B, Base of petals — near yellow — Group 13B, Reverse side of petals — near red — Group 54A.

*Sepals.*—Color outside near yellow-green Group 148A. Extending beyond the tip of the bud equal to about ¼ of its length. Some foliaceous appendages curl back as petals begin to unfurl. Color inside 148D.

*Peduncle.*—Length — medium. Aspect — few prickels. Strength — erect — strong. Color — near yellow-green — Group 147A.

Bloom:

*Size.*—Large from 5½ inches to 6 inches.

*Borne.*—Singly and several together.

*Form.*—Cupped at first, petals remaining at first loosely rolled outward becoming almost flat when fully open.

*Petalage.*—Double 25 to 35 petals.

*Color.*—During first 2 days inner petals at center of flower — near red Group 51B — Outer edge of petal near red — Group 51A. Outer petals — near red Group 51A. Outer edge of petal near red — Group 53C. Base of petals — near yellow Group 13B. Reverse of petals — near red — Group 51B with some shades of 54B. General tonality — from a distance — shades of red Group 54B to 54C, with outer edge of petals darkening in hot drier weather to shadings of 53D. Color changes — As bloom ages, near red Group 54C. General tonality — Same as above with color fading until petals drop.

*Petals.*—Texture — medium thick. Appearance — inside — velvety; outside — satiny. Form — round slightly notched. Arrangement — regularly arranged shingle like. Petaloids in center — few. Persistence — drop off cleanly. Fragrance — moderate to strong. Lasting quality — on plant — long. As cut flower — long.

REPRODUCTIVE ORGANS

Stamens: Arranged regularly about pistils.

Filaments: Most with anthers — color near yellow-orange Group 20A.

Anthers: Medium size — color near yellow-orange Group 22A.
Styles: Bunched — uneven lengths — thin.
Stigmas: Color — near yellow Group 13C.
Hips: Globular — flat top. Size — large. Color — near greyed-orange Group 169 D when mature. Seeds do not protrude. Seeds per hip — 20 to 25.

PLANT

Form: Upright.
Growth: Very vigorous.
Height attained: 6 to 8 ft.
Foliage: Compound of 3 to 5 leaflets.
*Size.*—Large.
*Quantity.*—Normal.
*Color.*—New foliage upper side near greyed purple Group 183A. Underside — near greyed purple group 183B. Old foliage: upper side — near yellow-green Group 147A. Underside — near greyed green Group 148C.
*Shape.*—Oval pointed.
*Texture.*—Upper side — thick leathery. Underside — thick dull.
*Edge.*—Serrated.
*Serration.*—Irregular.
*Leaf Stem.*—Color near yellow-green Group 146A. Under side near yellow-green Group 146B.

*Stipules.*—Medium length — some increasing in size with age.
*Resistance to disease.*—Blackspot — average. Mildew — average. Rust — average.
Wood:
*New wood.*—Color near yellow-green Group 146C. Bark smooth.
*Old wood.*—Color near yellow-green Group 148B. Bark moderately smooth.
*Thorns.*—Quantity on main stalks from base — average. On laterals from stalk — ordinary.
*Form.*—Short narrow base.
*Length.*—Medium length $\frac{3}{8}''$.
*Color (when young).*—Near greyed-orange Group 174B.
*Position.*—Irregular.
*Prickles.*—Quantity on main stalks — few on laterals.
*Winter hardiness.*—Average.

I claim:

1. A new and distinct variety of rose plant of the Hybrid Tea class substantially as herein shown and described, characterized particularly as to novelty by (1) blooms which display a spectrum of red shades ranging from a lighter hue at the petal base to a vibrant watermelon red on the petal edge which is particularly dramatic under sunny skies, and (2) a vigorous and erect growth habit.

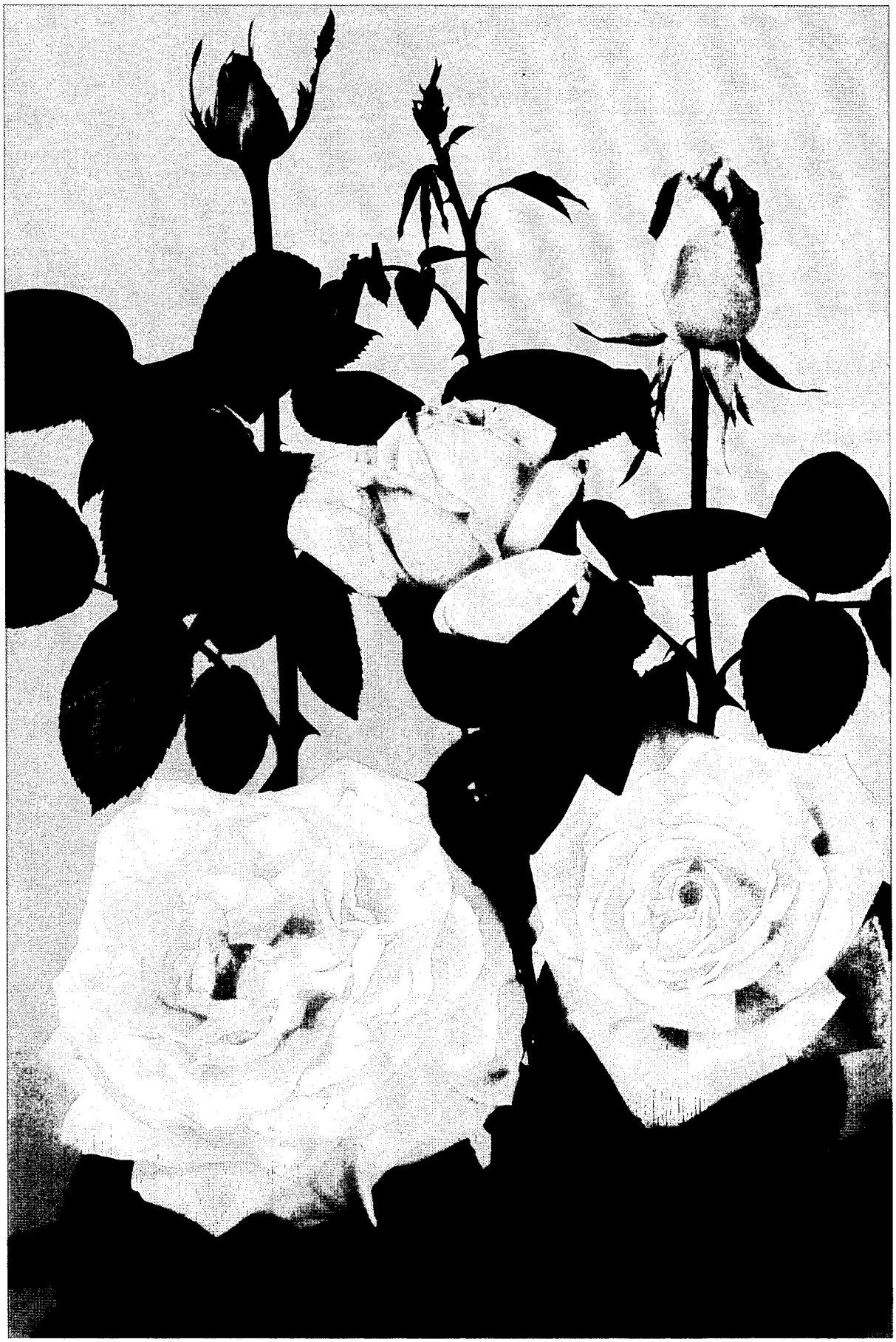

* * * * *